United States Patent [19]

Chiarino et al.

[11] Patent Number: 4,727,065
[45] Date of Patent: Feb. 23, 1988

[54] BIS-(2-AMMONIUM-2-HYDROXYMETHYL-1,3-PROPANEDIOL)(2R-CIS)-(3-METHYLOXIRANYL)-PHOSPHONATE, A METHOD OF PREPARING SAME, AND PHARMACEUTICAL COMPOSITIONS CONTAINING SAME

[75] Inventors: Dario Chiarino, Monza; Davide Della Bella; Vittorio Ferrari, both of Milan, all of Italy

[73] Assignee: Zambon S.p.A., Milan, Italy

[21] Appl. No.: 824,922

[22] Filed: Jan. 23, 1986

Related U.S. Application Data

[63] Continuation of Ser. No. 747,696, Jun. 24, 1985, abandoned, which is a continuation of Ser. No. 256,396, Apr. 22, 1981, abandoned, which is a continuation of Ser. No. 57,801, Jul. 16, 1979, abandoned.

[30] Foreign Application Priority Data

Jul. 19, 1978 [IT] Italy ............................ 25853 A/78

[51] Int. Cl.$^4$ ............................................. A61K 31/665
[52] U.S. Cl. ............................................................. 514/99
[58] Field of Search ............................................. 514/99

[56] References Cited

U.S. PATENT DOCUMENTS 3,641,063 2/1972 Miller ..................................... 514/99

Primary Examiner—Jerome D. Goldberg
Attorney, Agent, or Firm—Stevens, Davis, Miller & Mosher

[57] ABSTRACT

Bis-(2-ammonium-2-hydroxymethyl-1,3-propanediol)(2R-cis)-(3-methyloxiranyl)-phosphonate showing high bioavailability and tolerability is disclosed, as well as a method for preparing same from (2R-cis)-(3-methyloxiranyl)-phosphoric acid, or a salt thereof, and 2-amino-2-hydroxymethyl-1,3-propanediol, or a salt thereof. Pharmaceutical compositions containing the novel bis-phosphonate; useful for clinical forms of urinary and respiratory infections, are also disclosed.

4 Claims, No Drawings

BIS-(2-AMMONIUM-2-HYDROXYMETHYL-1,3-PROPANEDIOL(2R-CIS)-(3-METHYLOXIRANYL)-PHOSPHONATE, A METHOD OF PREPARING SAME, AND PHARMACEUTICAL COMPOSITIONS CONTAINING SAME

This application is a continuation of application Ser. No. 747,696 filed June 24, 1985, now abandoned, which in turn is a continuation of application Ser. No. 256,396 filed 4-22-81, now abandoned, which in turn is a continuation of application Ser. No. 057,801 filed 7-16-79, now abandoned.

The present invention relates to a new salt of (2R-cis)-(3-methyloxiranyl)-phosphonic acid and to the preparation thereof.

More particularly, the present invention relates to the bis-(2-ammonium-2-hydroxymethyl-1,3-propanediol) (2R-cis)-(3-methyloxiranyl)-phosphonate of the formula

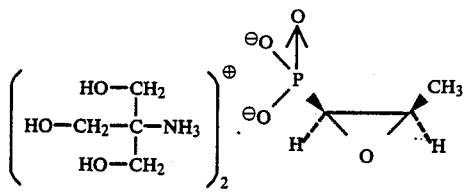

and to its preparation, as well as pharmaceutical compositions containing same.

The (2R-cis)-(3-methyloxiranyl)-phosphonic acid, whose common name is Fosfomycin (Merck Index-9th Edition-4110), will for brevity be indicated also by this name hereinafter. Fosfomycin sodium and calcium salts are widely used in the human and veterinary field to inhibit the growing of gram-positive and gram-negative pathogenous bacteria.

The Fosfomycin salt according to the present invention, the bis-(2-ammonium-2-hydroxymethyl-1,3-propanediol) (2R-cis)-(3-methyloxiranyl)-phosphonate, has proved to have both a tolerability and a bioavailability remarkably more favorable than those of the Fosfomycin sodium and calcium salts.

More particularly, the bioavailability of the Fosfomycin salt of the present invention in man has been proved to be at least 200% (i.e. double) in comparison with that of the other salts of Fosfomycin both in terms of cumulative urinary recovery of active antibiotic and in terms of area under the blood level versus time curve.

The preparation of the Fosfomycin salt of this invention may be carried out according to methods generally used in chemistry and per se well known to those skilled in the art. For instance, it may be prepared by a double exchange reaction between the monohydrated calcium salt of the (2R-cis)-(3-methyloxiranyl)phosphonic acid and the oxalate of the 2-amino-2-hydroxymethyl-1,3-propanediol.

The preparation of the salt of the present invention is illustrated in the following example, which however does not limit the invention in any way.

EXAMPLE

To 105.9 g of the monohydrated calcium salt of the (2R-cis)-(3-methyloxiranyl)-phosphonic acid suspended in 320 ml water at 60° C., and under stirring, a solution consisting of 145 g of 2-amino-2-hydroxymethyl-1,3-propanediol and 49 g of oxalic acid in 270 ml water was gradually added.

The resulting suspension was allowed to cool to room temperature while continuing the stirring for seven hours.

After staying overnight at 4° C., under stirring, the suspension was filtered off under vacuum on Theorite 5 (trademark of Seitz-Filter-Werke for a commercial filtering material) whereupon the filtrate was evaporated to dryness.

The residue was treated with 500 ml absolute ethyl alcohol and refluxed, under stirring, for one hour.

The white crystalline product which separates after cooling was collected by filtration under vacuum and dried for 10 hours at 60° C. under vacuum.

185 g of bis-(2-ammonium-2-hydroxymethyl-1,3-propanediol) (2R-cis)-(3-methyloxiranyl)-phosphonate were thus obtained (m.p. = 146°–148° C.).

Elemental analysis gave the following results:

| | | C | H | N |
|---|---|---|---|---|
| for $C_{11}H_{29}N_2O_{10}P$ | found % | 34.55 | 7.64 | 7.20 |
| $[\alpha]_D^{20} = -3.3°$ (C = 10%). | calculated % | 34.74 | 7.69 | 7.37 |

The indications are that the product of the present invention is useful for treating infections due to gram-positive and gram-negative bacteria that are sensitive to Fosfomycin. It is particularly indicated for all clinical forms of urinary and respiratory infections.

The product of the present invention may be administered orally or parenterally.

For oral administration (sachets):

The compositions for oral administration corresponding to 250 mg, 500 mg and 2000 mg of the conventional Fosfomycin are shown in the following table, where parts are given in grams:

| | | | |
|---|---|---|---|
| Bis-(2-ammonium-2-hydroxymethyl-1,3-propanediol)(2R—cis)-(3-methyloxiranyl)-phosphonate | 0.675 | 1.350 | 5.400 |
| Sodium Carboxymethylcellulose | 0.080 | 0.100 | 0.120 |
| Lactose | 0.050 | 0.100 | 0.300 |
| Titanium Dioxide | 0.050 | 0.070 | 0.100 |
| Orange Flavor | 0.050 | 0.050 | 0.080 |
| Saccharose | 2.095 | 2.330 | 4.000 |

For parenteral administration, each package contains a vial plus an ampoule of sterile water for use as solvent. Each vial contains 675 mg, 1350 mg or 2700 mg of the compound of the present invention, in form of a sterile powder. No non-active ingredient is added. When it is time for administration, the sterile powder is dissolved with the sterile water. The solvent quantities are 2.5 ml of solvent per each vial containing 675 or 1350 mg of the new compound and 5.0 ml per each vial containing 2700 mg of the new compound.

What is claimed is:

1. A pharmaceutical composition for oral administration containing from 675 to 5400 mg of a substantially pure bis-(2-ammonium-2-hydroxymethyl-1,3-propanediol)(2R-cis)-(3-methyloxiranyl)-phosphonate in admixture with an inert carrier, said composition being effective against infections due to gram-positive and gram-negative bacteria.

2. A solid pharmaceutical composition for oral administration containing from 675 to 5400 mg of a substantially pure bis-(2-ammonium-2-hydroxymethyl-1,3- propanediol)(2-R-cis)-(3-methyloxiranyl)-phosphonate in admixture with an inert carrier, said composition being effective against infections due to gram-positive and gram-negative bacteria.

3. An improved method for treating infections in man; due to gram-positive and gram-negative pathogenic bacteria, comprising subjecting said bacteria to a composition, administered orally, containing an effective growth-inhibiting amount of a salt which is a substantially pure bis(2-ammonium-2-hydroxymethyl-1.3-propanediol)(2R-cis)-(3-methyloxiranyl)phosphonate.

4. An improved method as defined in claim 3 in which the salt is present in the composition in association with a pharmaceutically-acceptable inert carrier or diluent.

* * * * *